(12) United States Patent
Grobbee et al.

(10) Patent No.: US 9,055,993 B2
(45) Date of Patent: Jun. 16, 2015

(54) DENTURE REFERENCE AND REGISTRATION SYSTEM

(71) Applicant: Global Dental Science, LLC, Scottsdale, AZ (US)

(72) Inventors: Johannes Petrus Michael Grobbee, Oosterbeek (NL); Jerry Gaubert, Phoenix, AZ (US)

(73) Assignee: Global Dental Science LLC, Scottsdale, AZ (US)

( * ) Notice: Subject to any disclaimer, the term of this patent is extended or adjusted under 35 U.S.C. 154(b) by 19 days.

(21) Appl. No.: 14/013,295

(22) Filed: Aug. 29, 2013

(65) Prior Publication Data

US 2015/0064653 A1   Mar. 5, 2015

(51) Int. Cl.
*A61C 8/00* (2006.01)
*A61C 13/265* (2006.01)

(52) U.S. Cl.
CPC ........... *A61C 13/2656* (2013.01); *A61C 8/0048* (2013.01); *A61C 8/0068* (2013.01); *A61C 8/0095* (2013.01)

(58) Field of Classification Search
CPC .................................................... A61C 8/0048
USPC ......................................................... 433/172
See application file for complete search history.

(56) References Cited

U.S. PATENT DOCUMENTS

| | | |
|---|---|---|
| 200,445 A | 2/1878 | Fahnestock |
| 321,847 A | 7/1885 | Peirce et al. |
| 711,324 A | 10/1902 | Lacy |
| 1,223,450 A | 4/1917 | Van Allen |
| 1,293,627 A | 2/1919 | Bowers |
| 1,585,348 A | 5/1926 | Hick et al. |
| 1,652,910 A | 12/1927 | Psayla |
| 1,714,185 A | 5/1929 | Hugh |
| 1,863,591 A | 6/1932 | Crowell |
| 1,914,606 A | 6/1933 | Kinna et al. |
| 2,107,181 A | 2/1938 | Guyton |
| 2,418,833 A | 4/1947 | Harris et al. |
| 2,472,492 A | 6/1949 | Saffir |
| 2,641,835 A | 6/1953 | Greenmun |

(Continued)

FOREIGN PATENT DOCUMENTS

| | | |
|---|---|---|
| JP | 2008307281 | 12/2008 |
| WO | 2001032096 | 12/2001 |

(Continued)

OTHER PUBLICATIONS

USPTO; Notice of Allowance dated Jun. 6, 2014 in U.S. Appl. No. 13/249,210.

(Continued)

*Primary Examiner* — Ralph Lewis
(74) *Attorney, Agent, or Firm* — Snell & Wilmer L.L.P.

(57) ABSTRACT

An improved denture system is disclosed. An improved denture system has a support bar and an artificial denture base. The denture base has an oversize cutout and a corresponding cavity and the support bar has a plurality of reference posts which mechanically interface with the corresponding cavity so that the support bar is connected to the artificial denture base and provides reinforcement and stability to the denture system. The shape and position of the reference posts fully constrains the support bar in a fixed position with reference to the denture base. In one embodiment, the denture base snap-fits onto the support bar.

19 Claims, 23 Drawing Sheets

(56) References Cited

U.S. PATENT DOCUMENTS

| | | | |
|---|---|---|---|
| 2,985,961 A | 5/1961 | Schwartz | |
| 2,994,957 A | 8/1961 | Mcleod | |
| 3,083,459 A | 4/1963 | McMurry et al. | |
| 3,241,238 A | 3/1966 | Kertsten | |
| 3,644,996 A | 2/1972 | Weinkle | |
| 3,667,123 A | 6/1972 | Huey | |
| 3,727,309 A | 4/1973 | Huey | |
| 3,748,739 A * | 7/1973 | Thibert | 433/173 |
| 3,813,777 A | 6/1974 | Van Handel et al. | |
| 4,029,632 A | 6/1977 | Gross et al. | |
| 4,227,877 A | 10/1980 | Tureaud et al. | |
| 4,247,287 A | 1/1981 | Gigante | |
| 4,299,573 A | 11/1981 | Ricci | |
| 4,533,325 A | 8/1985 | Blair et al. | |
| 4,591,341 A | 5/1986 | Andrews | |
| 4,634,377 A | 1/1987 | Behrend | |
| 4,784,608 A * | 11/1988 | Mays | 433/172 |
| 4,931,016 A | 6/1990 | Sillard | |
| 5,098,296 A | 3/1992 | Cullen | |
| 5,151,044 A | 9/1992 | Rotsaert | |
| 5,188,529 A | 2/1993 | Luth | |
| 5,427,906 A * | 6/1995 | Hansen | 433/173 |
| 5,672,305 A | 9/1997 | Kogure | |
| 5,711,668 A | 1/1998 | Huestis | |
| 5,716,214 A * | 2/1998 | Lund et al. | 433/173 |
| 5,718,584 A | 2/1998 | Wong | |
| 5,833,461 A | 11/1998 | Wong | |
| 5,839,900 A | 11/1998 | Billet et al. | |
| 6,056,547 A * | 5/2000 | Names | 433/173 |
| 6,139,322 A | 10/2000 | Liu | |
| 6,149,427 A | 11/2000 | Van Handel | |
| 6,224,372 B1 | 5/2001 | Ibsen et al. | |
| 6,227,851 B1 | 5/2001 | Chishti et al. | |
| 6,384,107 B2 | 5/2002 | Liu | |
| 6,422,864 B1 | 7/2002 | Glatt | |
| 6,488,503 B1 | 12/2002 | Lichkus et al. | |
| 6,616,444 B2 | 9/2003 | Andreiko et al. | |
| 6,851,949 B1 | 2/2005 | Sachdeva | |
| 7,021,934 B2 * | 4/2006 | Aravena | 433/173 |
| 7,153,135 B1 | 12/2006 | Thomas | |
| 7,234,940 B2 | 6/2007 | Weissman | |
| 7,433,810 B2 | 10/2008 | Pavloskaia et al. | |
| 7,474,932 B2 | 1/2009 | Geng | |
| 7,758,345 B1 | 7/2010 | Christensen | |
| 8,043,091 B2 | 10/2011 | Schmitt | |
| 8,348,669 B1 | 1/2013 | Schmitt | |
| 8,567,408 B2 | 10/2013 | Roettger et al. | |
| 8,641,938 B2 | 2/2014 | Howe | |
| 8,801,431 B2 | 8/2014 | Thompson | |
| 2002/0180760 A1 | 12/2002 | Rubbert et al. | |
| 2003/0108845 A1* | 6/2003 | Giovannone et al. | 433/173 |
| 2003/0162147 A1 | 8/2003 | Dequeker | |
| 2003/0211444 A1 | 11/2003 | Andrews | |
| 2004/0005530 A1* | 1/2004 | Mullaly et al. | 433/172 |
| 2004/0219490 A1 | 11/2004 | Gartner et al. | |
| 2005/0175957 A1 | 8/2005 | Haje | |
| 2005/0186539 A1 | 8/2005 | McLean et al. | |
| 2005/0284489 A1 | 12/2005 | Ambis | |
| 2006/0040232 A1 | 2/2006 | Shoup | |
| 2006/0040236 A1 | 2/2006 | Schmitt | |
| 2006/0210945 A1 | 9/2006 | Savic et al. | |
| 2006/0286507 A1 | 12/2006 | Dequeker | |
| 2007/0231774 A1 | 10/2007 | Massad | |
| 2008/0085489 A1 | 4/2008 | Schmitt | |
| 2008/0090207 A1 | 4/2008 | Rubbert | |
| 2008/0127698 A1 | 6/2008 | Luckey et al. | |
| 2008/0206710 A1 | 8/2008 | Kruth et al. | |
| 2008/0206714 A1 | 8/2008 | Schmitt | |
| 2008/0209974 A1 | 9/2008 | Ewolski et al. | |
| 2008/0300716 A1 | 12/2008 | Kopelman | |
| 2009/0148813 A1 | 6/2009 | Sun et al. | |
| 2009/0287332 A1 | 11/2009 | Adusumilli et al. | |
| 2009/0291407 A1 | 11/2009 | Kuo | |
| 2009/0325125 A1 | 12/2009 | Diangelo et al. | |
| 2010/0015572 A1 | 1/2010 | Dirkes et al. | |
| 2010/0062394 A1 | 3/2010 | Jones et al. | |
| 2010/0086186 A1 | 4/2010 | Zug et al. | |
| 2010/0094446 A1 | 4/2010 | Baloch et al. | |
| 2010/0324875 A1 | 12/2010 | Kalili | |
| 2011/0045442 A1 | 2/2011 | Adusimilli | |
| 2011/0112804 A1 | 5/2011 | Chishti et al. | |
| 2011/0129796 A1 | 6/2011 | Riggio | |
| 2011/0236856 A1 | 9/2011 | Kanazawa et al. | |
| 2011/0244417 A1 | 10/2011 | Hilsen et al. | |
| 2012/0058449 A1* | 3/2012 | Sklarski et al. | 433/173 |
| 2012/0178045 A1 | 7/2012 | Massad | |
| 2012/0179281 A1 | 7/2012 | Steingart et al. | |
| 2012/0258426 A1 | 10/2012 | Boe | |
| 2012/0285019 A1 | 11/2012 | Schechner et al. | |
| 2012/0329008 A1 | 12/2012 | Fishman et al. | |
| 2013/0108988 A1 | 5/2013 | Simoncic | |
| 2013/0209962 A1 | 8/2013 | Thompson et al. | |
| 2013/0216978 A1 | 8/2013 | Thompson et al. | |
| 2013/0218532 A1 | 8/2013 | Thompson et al. | |
| 2013/0249132 A1 | 9/2013 | Thompson | |
| 2013/0280672 A1 | 10/2013 | Thompson | |
| 2013/0316302 A1 | 11/2013 | Fisker | |
| 2014/0045967 A1 | 2/2014 | Thomas et al. | |
| 2014/0272796 A1 | 9/2014 | Grobbee et al. | |
| 2015/0037760 A1 | 2/2015 | Thompson et al. | |
| 2015/0064653 A1 | 3/2015 | Grobbee et al. | |

FOREIGN PATENT DOCUMENTS

| | | |
|---|---|---|
| WO | 2009105661 | 8/2009 |
| WO | 2009105700 | 8/2009 |
| WO | 2010022479 | 3/2010 |
| WO | 2012041329 | 4/2012 |
| WO | 2012061652 | 5/2012 |
| WO | 2012061655 | 5/2012 |
| WO | 2012061659 | 5/2012 |
| WO | 2012061660 | 5/2012 |
| WO | 2014130536 | 8/2014 |
| WO | 2015031062 | 3/2015 |

OTHER PUBLICATIONS

USPTO; Non-Final Office Action dated Jun. 6, 2014 in U.S. Appl. No. 13/823,466.

USPTO; Non-Final Office Action dated Jun. 20, 2014 in U.S. Appl. No. 13/830,963.

USPTO; Restriction Requirement dated Jul. 2, 2014 in U.S. Appl. No. 14/195,348.

EPO; European Search Report and Opinion dated Mar. 3, 2014 in Application No. 11838843.8.

PCT; International Search Report and Written Opinion dated Jul. 25, 2014 in Application No. PCT/US2014/017136.

PCT: International Search Report and Written Opinion dated Jul. 18, 2012 in Application No. PCT/US2011/059230.

PCT: International Preliminary Report on Patentability dated May 8, 2013 in Application No. PCT/US2011/059230.

PCT: International Search Report and Written Opinion dated Jul. 18, 2012 in Application No. PCT/US2011/059235.

PCT; International Preliminary Report on Patentability dated May 8, 2013 in Application No. PCT/US2011/059235.

PCT; International Search Report and Written Opinion dated Jul. 9, 2012 in Application No. PCT/US2011/059239.

PCT; International Preliminary Report on Patentability dated May 8, 2013 in Application No. PCT/US2011/059239.

PCT; International Search Report and Written Opinion dated Jul. 18, 2012 in Application No. PCT/US2011/059240.

PCT; International Preliminary Report on Patentability dated May 8, 2013 in Application No. PCT/US2011/059240.

USPTO; Restriction Requirement dated Sep. 5, 2014 in U.S. Appl. No. 13/823,621.

USPTO; Office Action dated Aug. 21, 2014 in U.S. Appl. No. 14/195,348.

USPTO; Final Office Action dated Oct. 21, 2014 in U.S. Appl. No. 14/195,348.

PCT; International Search Report and Written Opinion dated Aug. 7, 2014 in Application No. PCT/US2014/023654.

(56) References Cited

OTHER PUBLICATIONS

USPTO; Final Office Action dated Mar. 6, 2014 in U.S. Appl. No. 13/249,210.
USPTO; Restriction Requirement dated Dec. 23, 2013 in U.S. Appl. No. 13/823,466.
EPO; European Search Report dated Mar. 4, 2014 in Application No. 11838839.6.
USPTO; Office Action dated Sep. 24, 2013 in U.S. Appl. No. 13/249,210.
USPTO; Non-Final Office Action dated Oct. 23, 2014 in U.S. Appl. No. 13/823,621.
USPTO; Final Office Action dated dated Nov. 7, 2014 in U.S. Appl. No. 13/830,963.
USPTO; Office Action dated Jan. 5, 2015 in U.S. Appl. No. 12/939,136.
USPTO; Restriction Requirement dated Feb. 12, 2015 in U.S. Appl. No. 13/369,238.
USPTO; Advisory Action dated Feb. 23, 2015 in U.S. Appl. No. 13/830,963.
USPTO; Non-Final Office Action dated Apr. 9, 2015, U.S. Appl. No. 12/939,138.
USPTO; Notice of Allowance dated Apr. 13, 2015, U.S. Appl. No. 14/013,295.
USPTO; Final Office Action dated Mar. 26, 2015, U.S. Appl. No. 13/823,466.

* cited by examiner

DENTURE REFERENCE AND REGISTRATION SYSTEM

FIELD OF INVENTION

The present invention relates to implant and bar-supported or bar-retained dentures. More particularly, the present invention relates to a bar reference and registration system to place a bar in a CAD/CAM manufactured denture.

BACKGROUND OF THE INVENTION

In the field of dentures a metal bar on implants is used to stabilize the denture in the mouth and to strengthen the denture structure to avoid breakage.

In the traditional denture manufacturing process an impression is made of a patient's implants and edentulous or partially edentulous ridges. The impression is used to construct a plaster model of the patient's edentulous ridges and implants. A metal bar is manufactured to fit exactly on the plaster model, and to align with the patient's implants according to the implant analogs in the plaster model. The metal bar is installed on the plaster model and the denture structure is then built around the bar in wax. Artificial teeth are placed in the wax resulting in a complete wax up of the denture with the bar incorporated on top of a plaster model. Traditionally, the next step is to investment cast the wax into acrylic resin.

For example, with reference to FIGS. 1A and 1B, a prior art system 100 is illustrated. A plaster model 102 is made of a patient's dentition. A bar 104 is installed on the plaster model 102 via implant analog interfaces 106. Wax mockup 108 is molded by hand and is mechanically wrapped around the bar 104. Artificial teeth 110 are installed. To finalize the denture, the system 100 is processed using investment casting, thereby causing wax mockup 108 to be replaced with acrylic denture material.

More recently, dentures have been made using CAD/CAM technology, such as by milling or 3D printing. With CAD/CAM technology, the denture is made directly without using wax and plaster models, thus no plaster model having implant analogues is available to align and position the bar. Consequently, a cavity must be cut in the denture and the bar fitted into the cavity. However, the bar is often complex in shape and difficult to precisely and securely fit in the denture. For example, small discrepancies will occur if the full shape of the bar is used for reference and registration.

Furthermore, even if such a plaster model were made to assist with aligning and positioning the bar in the cavity, the fitting of the denture onto the bar is difficult and often imprecise because it is difficult to preserve the proper registration of the bar with respect to the denture while they are mated and the bar disconnected from the plaster model, particularly if the model impedes access to the cavity in the denture. Moreover, the production of such a model introduces unwanted delay and expense.

Thus, there exists a need for an improved reference and registration system to position the supporting bar in a denture made using CAD/CAM technology.

SUMMARY OF THE INVENTION

In accordance with various aspects of the present invention, an improved denture bar reference and registration system is provided. In accordance with an exemplary embodiment, an improved support bar comprising a plurality of implant interfaces and reference posts is inserted into an improved denture base having an oversize cutout and a corresponding cutout, wherein the corresponding cutout is configured to interface with the reference posts.

In one exemplary embodiment, any remaining opening between the bar and the denture is filled with denture resin.

In accordance with another exemplary embodiment, an improved support bar is accurately referenced and registered with respect to an improved denture base, yet is also readily removable, for example, by snap-fitting the base onto the bar.

BRIEF DESCRIPTION OF THE DRAWINGS

A more complete understanding of the present invention may be derived by referring to the detailed description and claims when considered in connection with the Figures, where like reference numbers refer to similar elements throughout the Figures, and:

DESCRIPTION OF THE EXEMPLARY EMBODIMENTS

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from the scope of the appended claims.

For the sake of brevity, conventional techniques for manufacturing and construction may not be described in detail herein. Furthermore, the connecting lines shown in various figures contained herein are intended to represent exemplary functional relationships and/or physical couplings between various elements. It should be noted that many alternative or additional functional relationships or physical connections may be present in a practical method of construction.

In accordance with various aspects of the present invention, an improved denture bar reference and registration system is provided. In accordance with an exemplary embodiment, an improved support bar comprising a plurality of implant interfaces and reference posts is inserted into an improved denture base having an oversize cutout and a corresponding cutout, wherein the corresponding cutout is configured to interface with reference posts, and as a result, securing the denture base or providing for easy positioning of the denture bar relative to the denture base and the system relative to the patient's edentulous ridges.

Securing the denture base, may in some example embodiments have multiple meanings or configurations. For example, "securing" can mean retaining the denture components, such as a denture system, a denture bar, or a denture base. Alternatively, "securing" may mean stabilizing the denture components, such as a denture system, a denture bar, or a denture base. Furthermore, "securing" may mean aligning the denture components, such as a denture system, a denture bar, or a denture base. Still furthermore, "securing" may mean reinforcing the denture or denture bar or denture base. In some embodiments "securing" may mean any combination of these meanings and configurations.

Figure 5A:
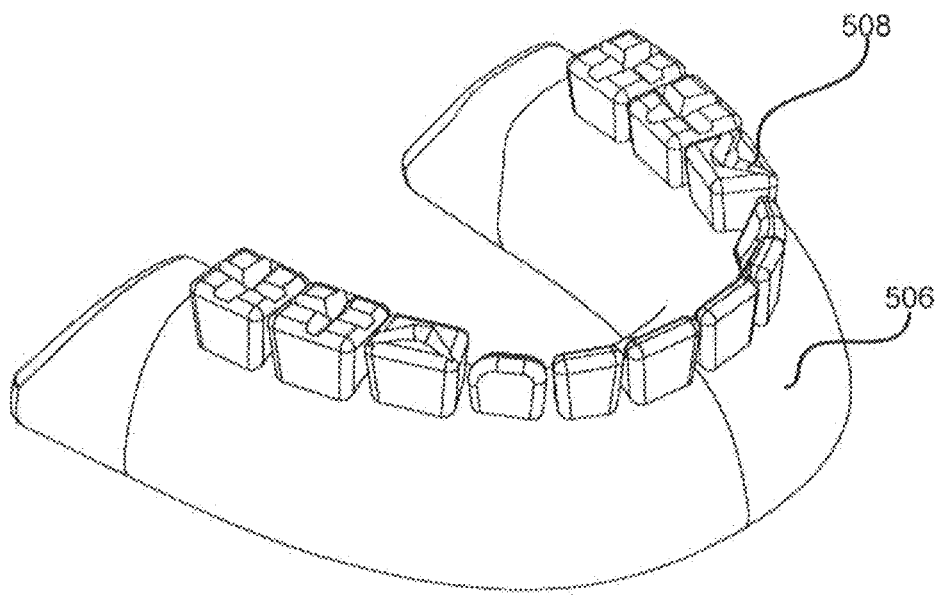
FIGS. 5A-5C are views of an exemplary embodiment of a denture base.
Figure 5B:
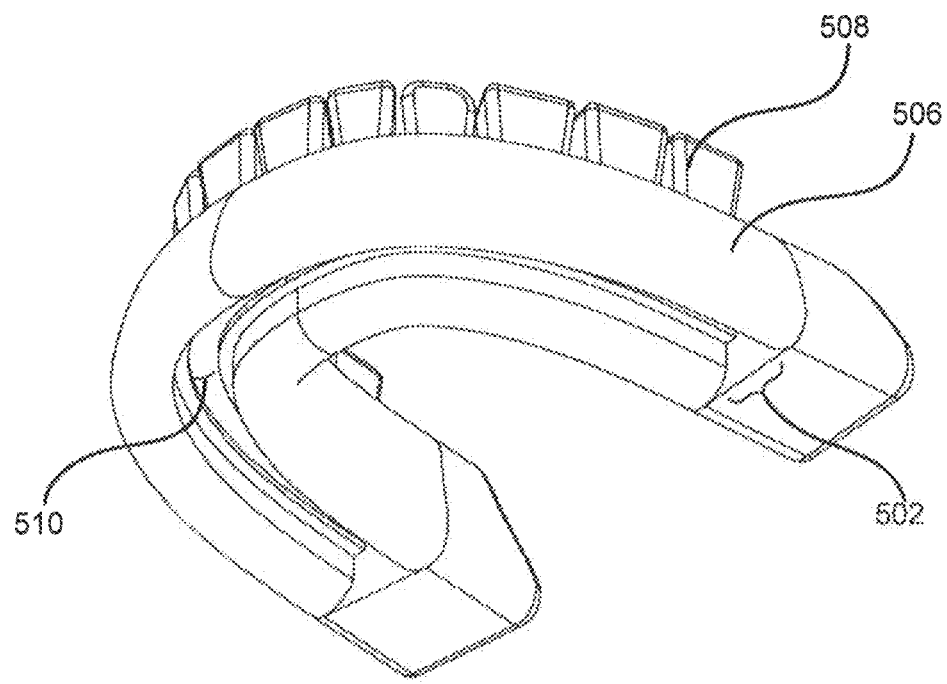
Figure 5C:
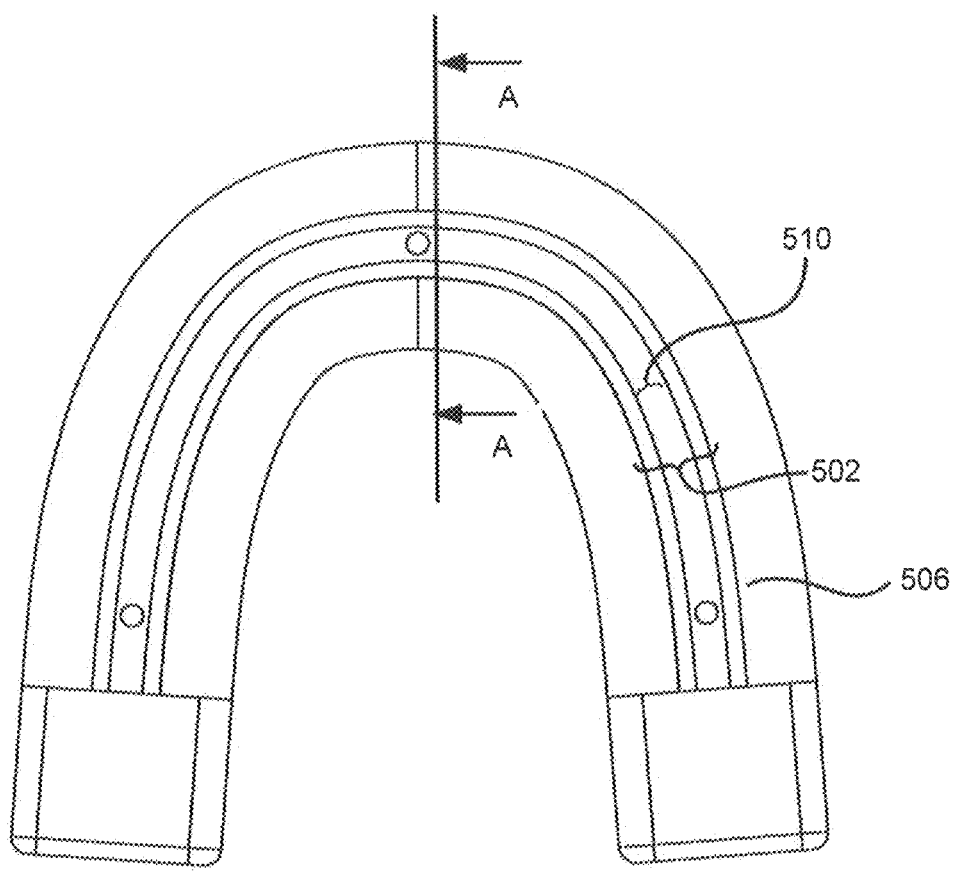
Figure 5D:
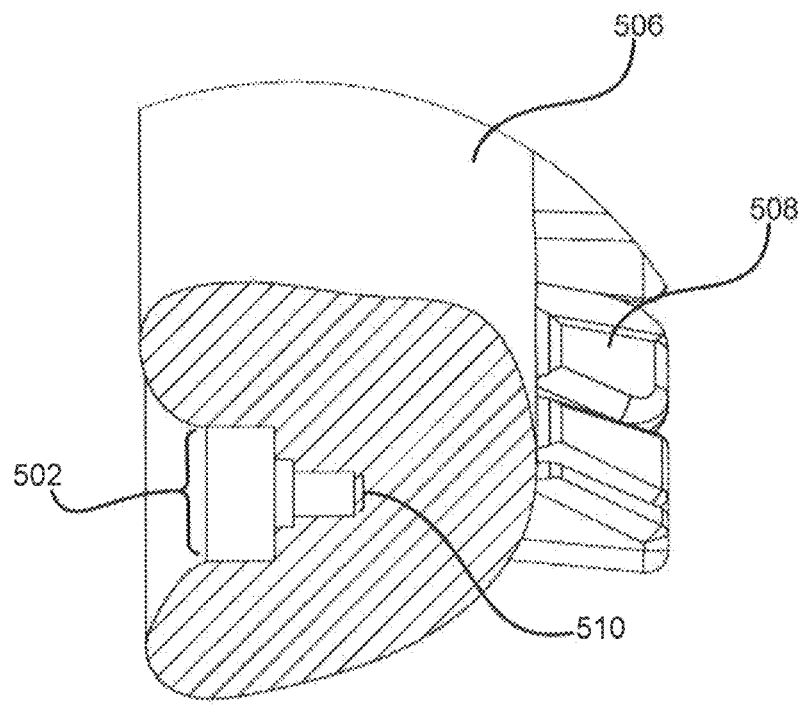
FIG. 5D is a section view A-A of an exemplary embodiment of a denture base according to FIG. 5C.
Figure 6A:
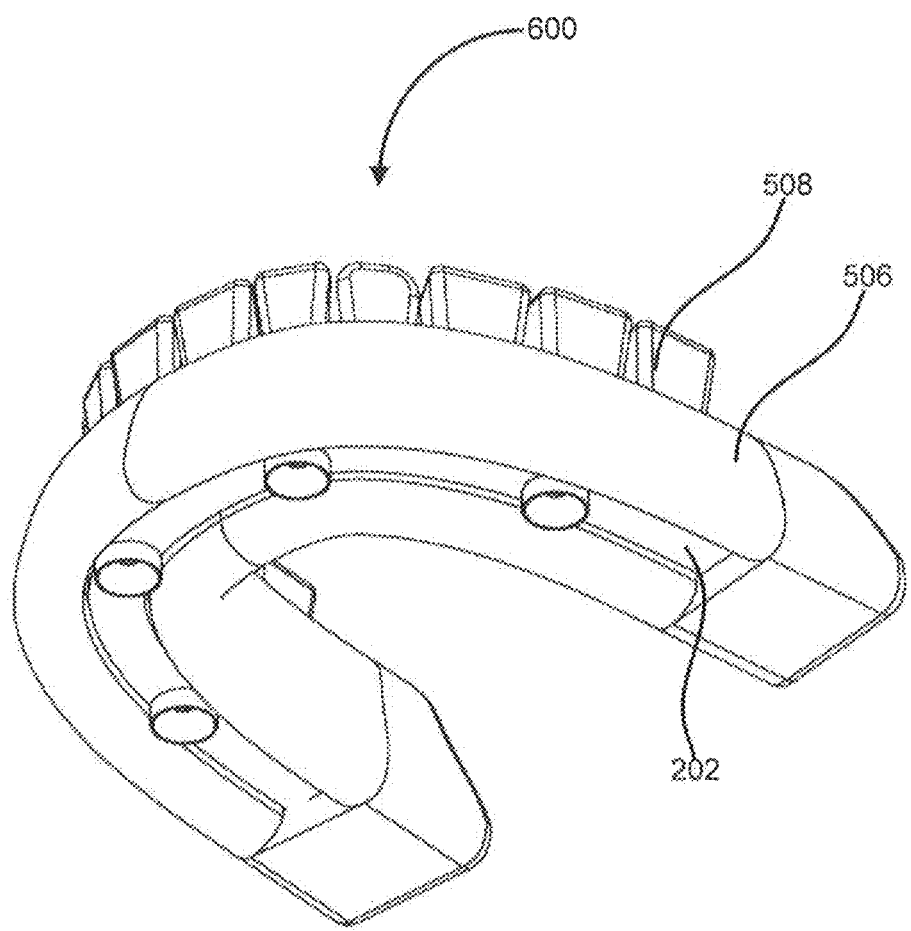
FIGS. 6A-6C are views of an exemplary embodiment of an improved denture having a support bar installed in a denture base.
Figure 6B:
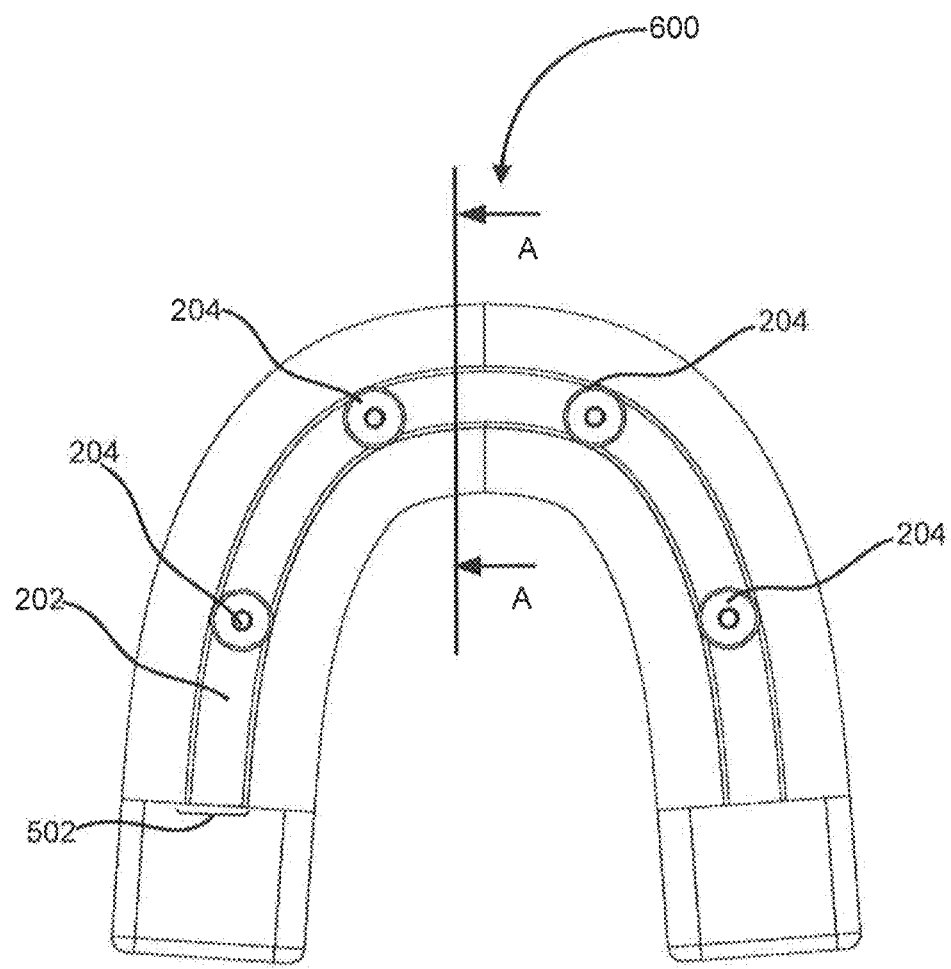
Figure 6C:
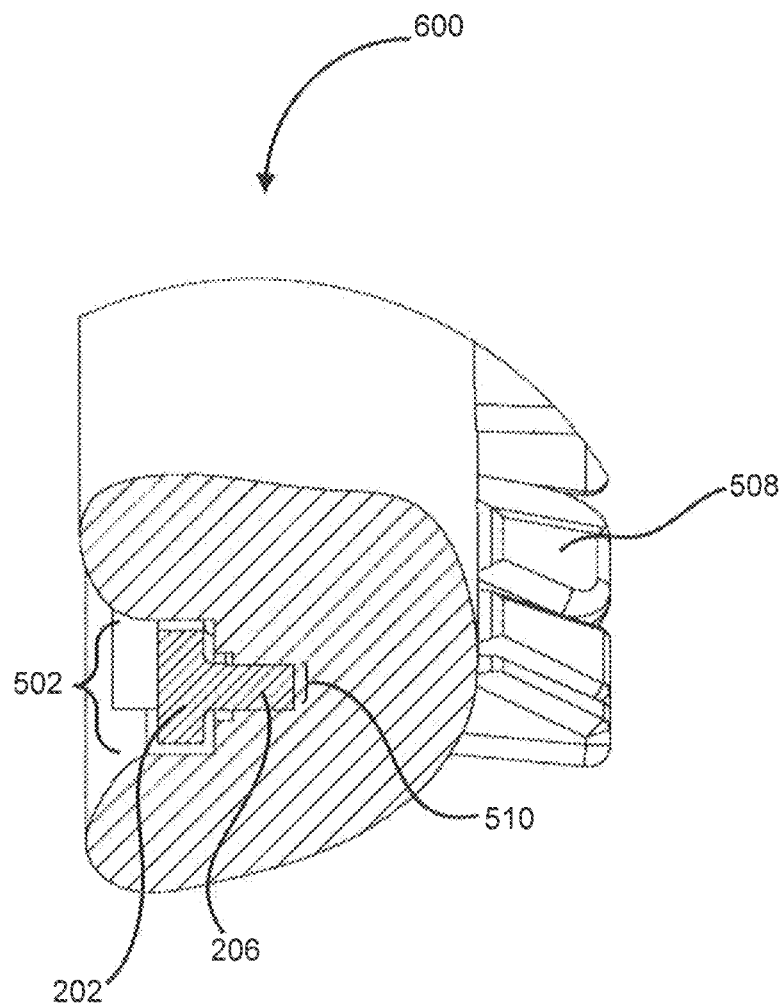

With reference to FIGS. 6A-6C, an improved denture system 600 is illustrated. Additionally with reference to FIGS. 2A-2C, 3A-3C, 5A-5D, improved denture system 600 has a support bar 202 and an artificial denture base 506. Support bar 202 has a plurality of reference posts 206 and a plurality of implant interfaces 204. Artificial denture base 506 has at least one oversize cutout 502 and at least one corresponding cavity 510. In one example embodiment, an oversize cutout 502 is a void in the artificial denture base 506 wherein contact between the profile of the bar 202 and the cutout 502 is limited in order to prevent unwanted overconstraint of the bar 202. For example, with reference to FIG. 6B, a gap is illustrated around the perimeter of bar 202 in oversize cutout 502. As illustrated with reference to FIGS. 5B, 5C, 6B, 6C, 7B and 10B, an oversize cutout may be a unitary channel that extends an entire length of the bar 202 with a gap around the perimeter so that the bar 202 only rests against the reference posts 206 and not against the oversize cutout. In one example embodiment, a corresponding cavity 510 is a void in the artificial denture base 506 extending farther into said denture base than said oversize cutout (see FIGS. 2A-C, 3A-C, 4A-B, 5C-D, 6A-C, 7B, 8, 9, and 10A-B) with location, shape, and dimensions selected so that a reference post 206 interfaces securely with the corresponding cavity 510 according to the disclosure herein.

Support bar 202 may be placed in oversize cutout 502. Reference post 206 may interface with corresponding cavity 510 so that support bar 202 is held in substantially fixed position, or is maintained, or otherwise coupled or retained in communication with the artificial denture base 506 or to otherwise secure the denture base 506 or providing for easy positioning of the denture bar 202 relative to the denture base 506 and the system relative to the patient's edentulous ridges.

Figure 1A:
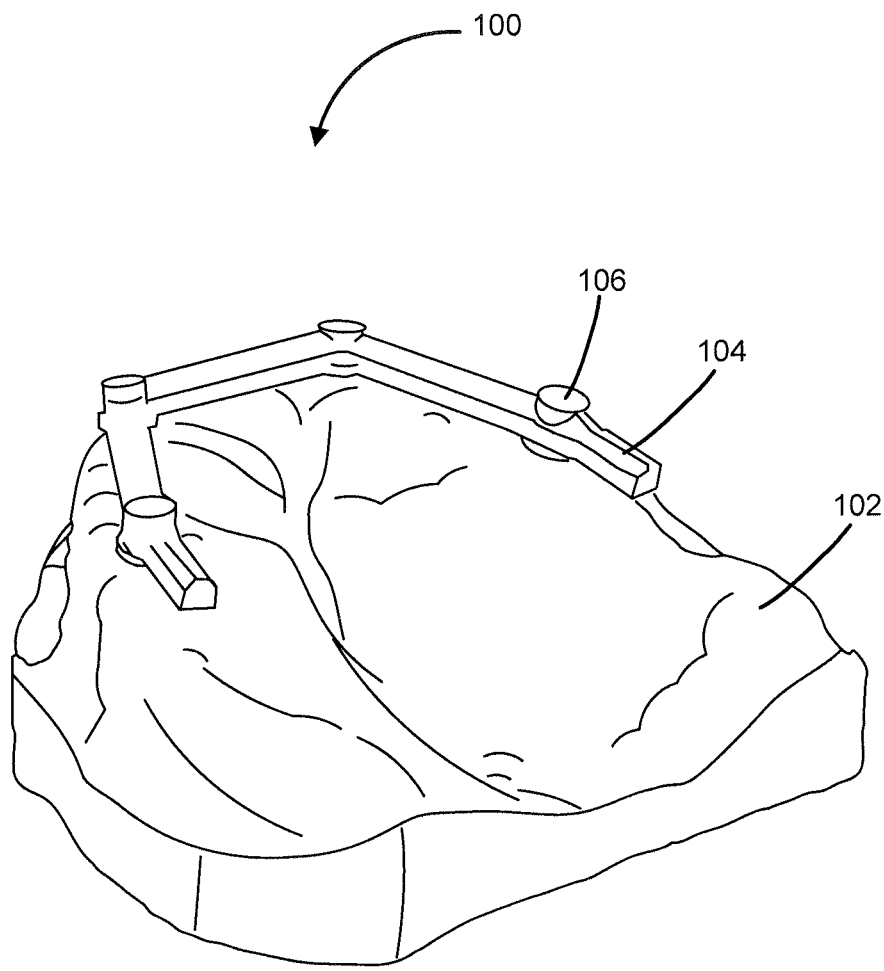
FIGS. 1A and 1B are views of a prior art system having a plaster model and a support bar.
Figure 1B:
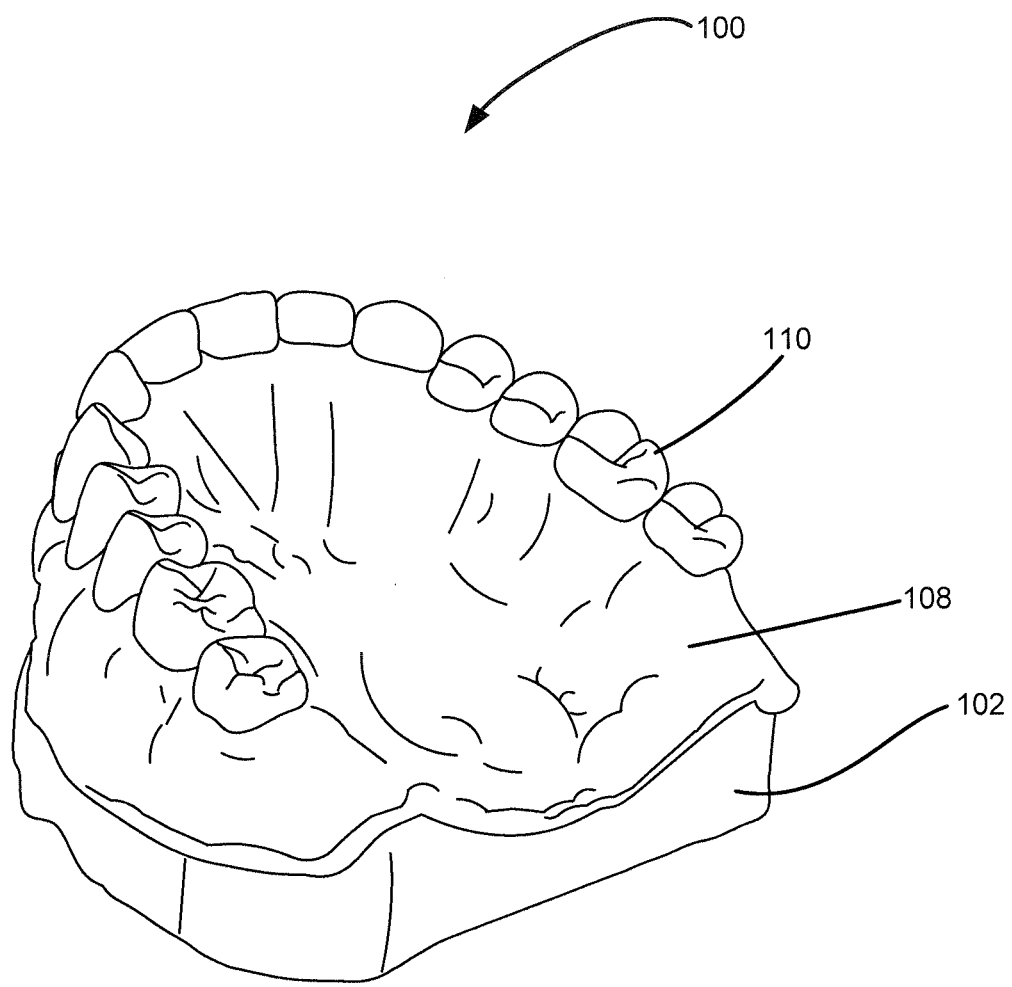
Figure 2A:
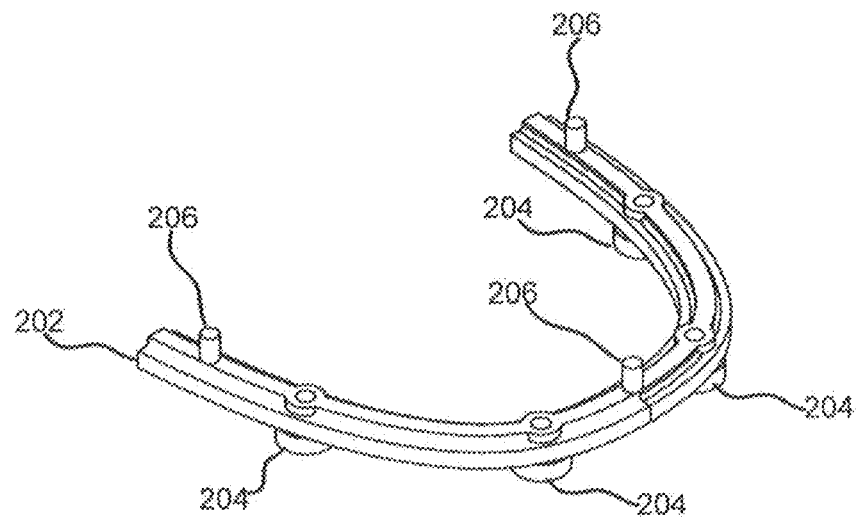
FIGS. 2A-2C are views of an exemplary embodiment of a support bar.
Figure 2B:
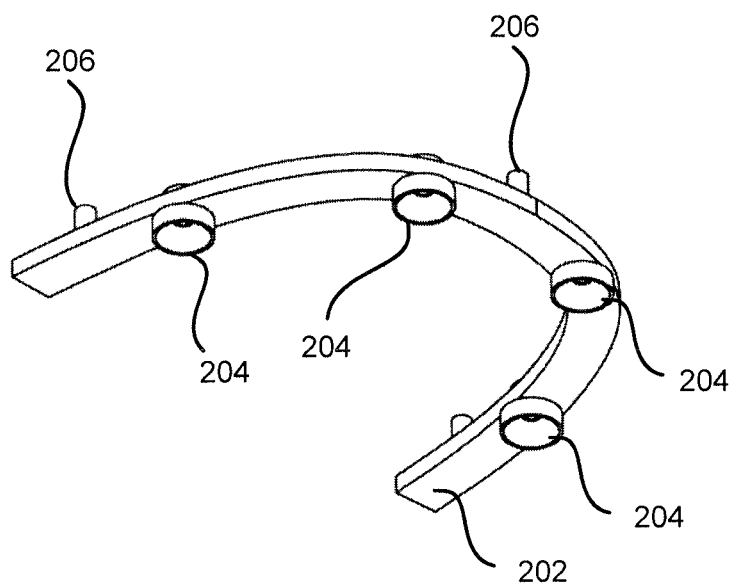
Figure 2C:
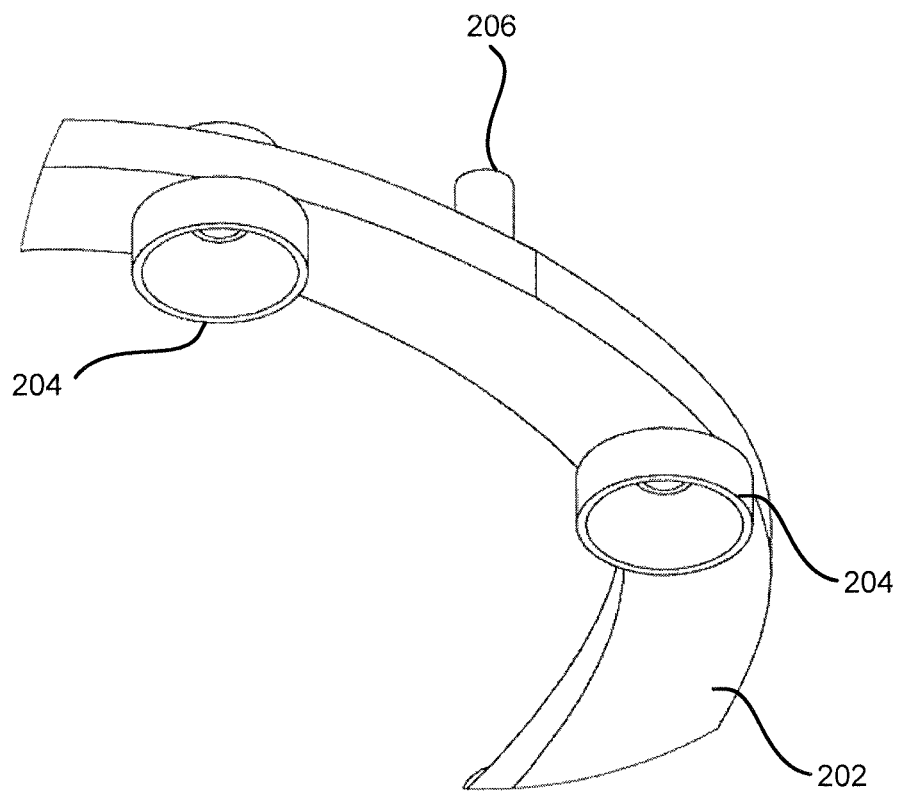
Figure 3A:
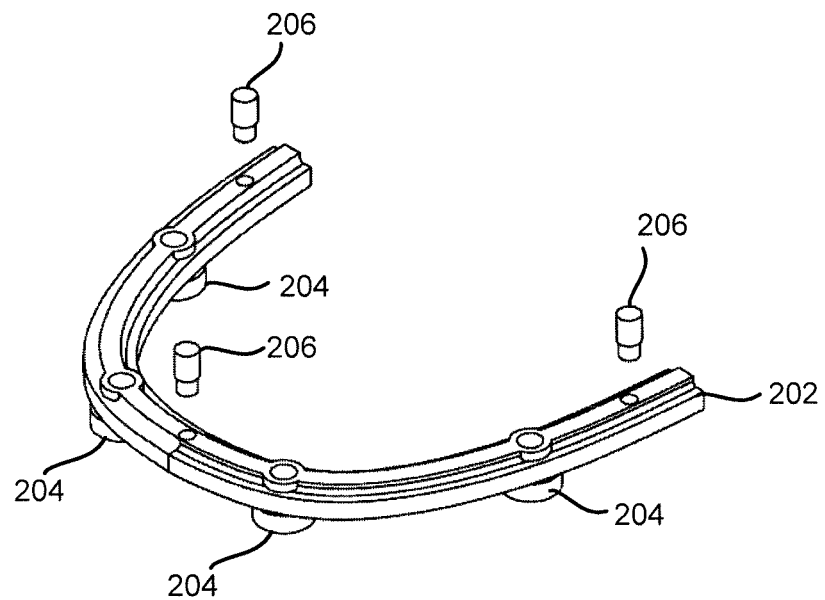
FIGS. 3A-3B are views of another exemplary embodiment of a support bar.
Figure 3B:
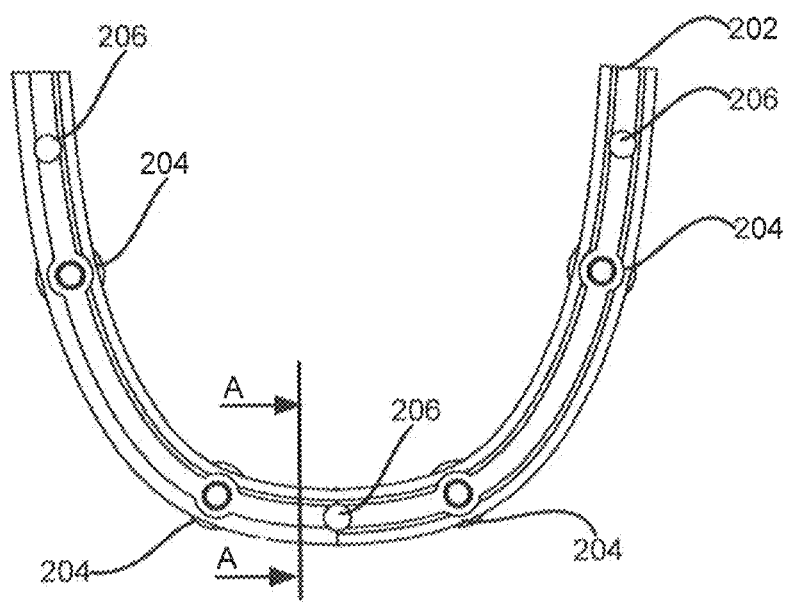
Figure 3C:
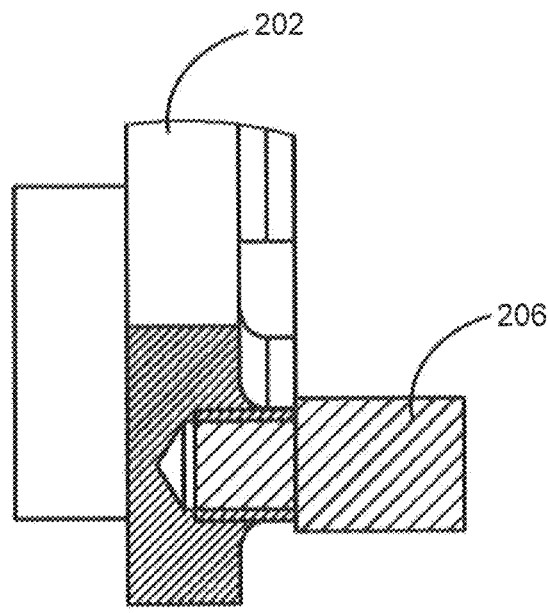
FIG. 3C is a section view A-A of an exemplary embodiment of a denture base having a support bar inserted into the denture according to FIG. 3B.
Figure 4A:
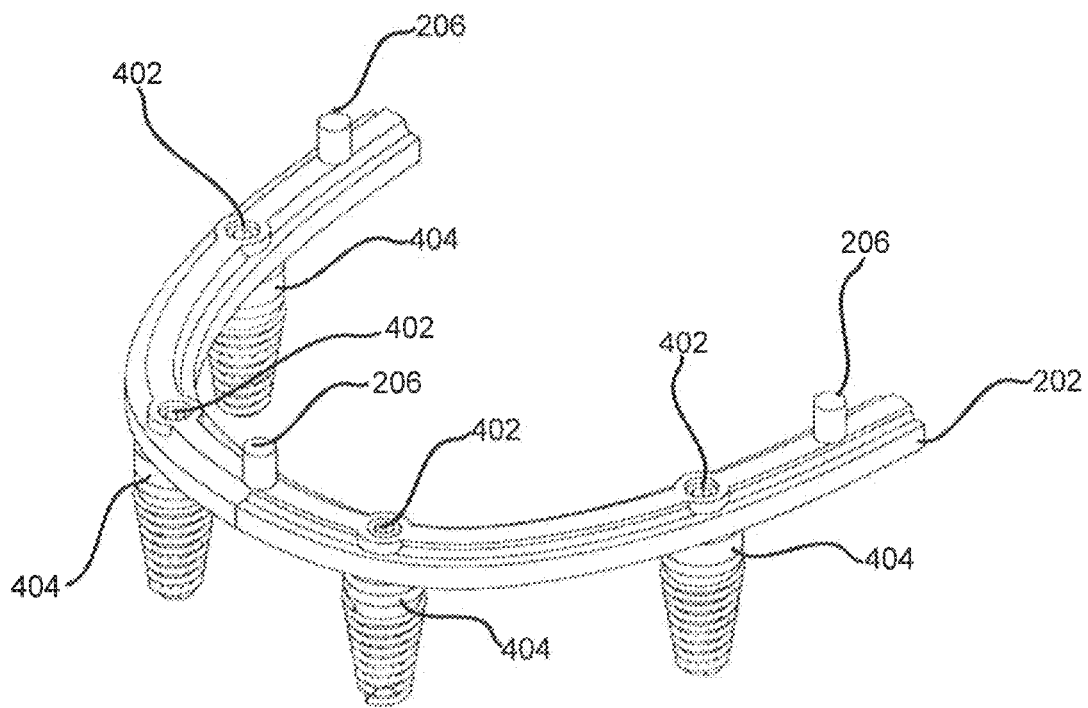
FIG. 4A is a view of an exemplary embodiment of a support bar mounted onto implants.
Figure 4B:
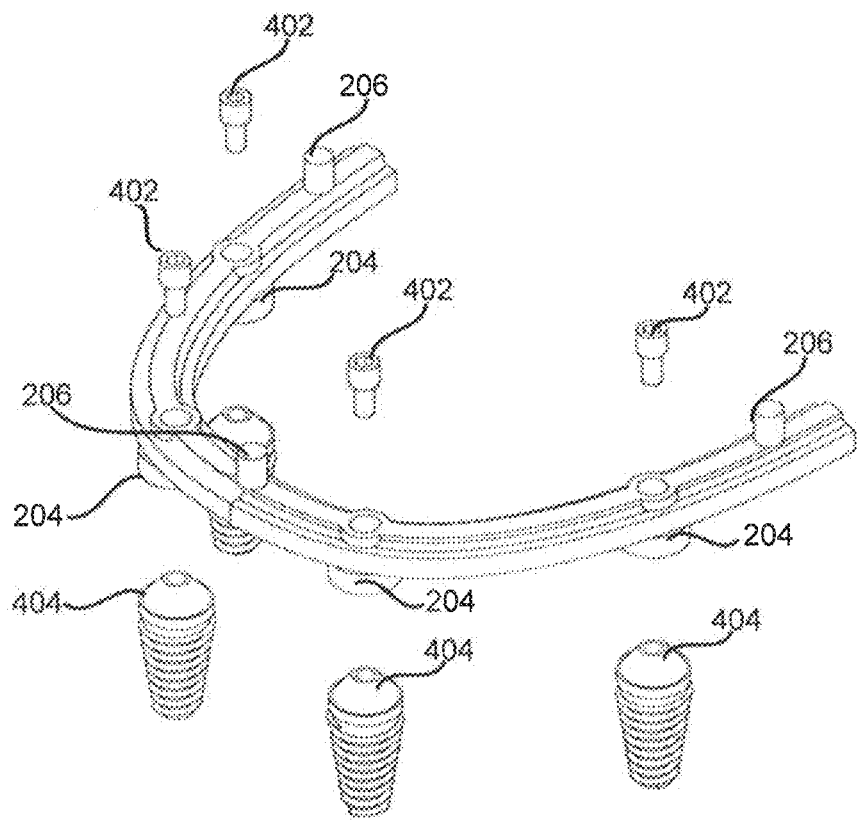
FIG. 4B is an exploded view of an exemplary embodiment of a support bar mounted onto implants according to FIG. 4A.

With reference to FIG. 2A-2C, a support bar 202 for use in an improved denture system 600 is illustrated. Support bar 202 may be made of joined segments to approximately follow the contour of a patient's edentulous ridges. Alternatively, support bar 202 may be segmented, or straight, or curved, or any other shape adapted to provide support to an improved denture system 600.

Support bar 202 may further comprise an implant interface 204 for connecting support bar 202 to a patient's implants 404. In one exemplary embodiment, a support bar 202 may comprise four implant interfaces 204. In another example embodiment, a support bar 202 may comprise six implant interfaces 204, or five implant interfaces 204, or three implant interfaces 204, or two implant interfaces 204, or one implant interface 204. In one embodiment, support bar 202 comprises implant interfaces 204 located at the joint of each segment of support bar 202. Alternatively, support bar 202 may comprise implant interfaces 204 spaced evenly along support bar 202. Still further, alternatively, support bar 202 may comprise implant interfaces 204 located at places corresponding to suitable sites along a patient's edentulous ridges for the installation of implants. Support bar 202 may comprise any number or configuration of implant interfaces 204 adapted to support an improved denture system 600. With momentary reference to FIGS. 4A-4B, generally, implant interface 204 comprises holes for insertion of fasteners 402 whereby support bar 202 is secured to a patient's implants 404. Alternatively, implant interface 204 may comprise captive olds, threaded holes, captive nuts, or any other fastening mechanism.

Support bar 202 may also comprise a plurality of reference posts 206. In one exemplary embodiment, each reference post 206 will extend into a corresponding cavity. For example, with momentary reference to FIGS. 5D and 6C and a corresponding cavity 510 in the artificial denture base 506, a reference post 206 may extend to retain the support bar 202 in position relative to the artificial denture base 506. The reference post 206 will typically be manufactured in one piece with the support bar 202, for example by machining or 3D printing. With momentary reference to FIGS. 3A-3C, in another embodiment, the reference posts 206 are manufactured separately and are attached to the support bar 202. For example, with reference to FIG. 3C, the reference posts 206 may be screwed, glued, snapped, or riveted to the support bar 202. In one embodiment, the support bar 202 is tapped and the reference posts 206 are threaded into the support bar 202. In another embodiment, the reference posts 206 are tapped and the support bar 202 is threaded into the reference posts 206. Alternatively, the reference posts 206 may be affixed by any other configuration or mechanism suitable for holding, maintaining, or otherwise coupling or retaining the support bar 202 in communication with reference posts 206.

Reference posts 206 may be any size or shape adapted to retain the support bar 202 in substantially fixed position relative to the artificial denture base 506. For example, with reference to FIG. 2A, in one embodiment reference posts 206 are circular. However, reference posts 206 can also be oval, or multisided, for example trapezoidal, heptagonal, hexagonal, septagonal, or octagonal or any other number of sides, or may be irregularly shaped, or may be T shaped or L shaped or may comprise any other shape or multiple reference posts may comprise different shapes such that the shape and position of the posts accomplish a fully constrained position of the support bar 202 when attached, joined, or otherwise connected with or coupled with the artificial denture base 506.

For example, in one embodiment, a fully constrained position of the support bar 202 is achieved by constraining the support bar 202 in a 3-2-1 registration by the interfacing of reference posts 206 and corresponding cavities 510. In this embodiment, the shape and position of the reference posts 206 create a plane, a line, and a point so that the support bar 202 is fully constrained in unique fixed position with reference to the artificial denture base 506. Alternatively, a fully constrained position of the support bar 202 may be achieved by constraining the support bar 202 in an RPS registration by the interfacing of reference posts 206 and corresponding cavities 510. In this embodiment, the shape and position of the reference posts 206 create numerous points so that the support bar 202 is fully constrained in unique fixed position with reference to the artificial denture base 506. Furthermore, best-fit registration, or any registration may be utilized that achieves a fully constrained position of the support bar 202 in unique fixed position with reference to the artificial denture base 506. Furthermore, in some embodiments, further alternative registration configurations may be utilized to achieve a unique fixed position of the support bar 202 with reference to the artificial denture base 506.

In one exemplary embodiment, a support bar 202 may be constrained by one reference post 206. In another example embodiment, a support bar 202 may be constrained by two reference posts 206, or may be constrained by three reference posts 206, or may be constrained by four reference posts 206, or may be constrained by a reference post 206 located at the joint of each segment of support bar 202. Alternatively support bar 202 may comprise reference posts 206 spaced evenly along support bar 202. Still further, alternatively, support bar 202 may comprise reference posts 206 located at places corresponding to suitable sites along the support bar 202 to avoid interfering with the location of implant interfaces 204. Support bar 202 may comprise any number or configuration of reference posts 206 adapted to fully constrain support bar 202 in unique substantially fixed position with reference to the artificial denture base 506. In some embodiments, the support bar 202 is overconstrained, for example, by using additional reference posts 206. In other embodiments, the support bar 202 is not overconstrained due to the potential for reduced stability of an overconstrained support bar 202 due to manufacturing tolerances among the overconstraining reference posts 206. However, in other exemplary embodiments, the support bar 202 is overconstrained without problem due to the sufficiently tight manufacturing tolerances. For example, with reference to FIGS. 8-10, in a support bar 202 interfaced with artificial denture base 506 via a snap-fit portion 802, the support bar 202 may be overconstrained.

Various materials may be used to manufacture support bar 202. In one exemplary embodiment, support bar 202 may comprise metal, such as titanium, aluminum or stainless steel, though it may alternatively comprise numerous other materials configured to provide support, such as, for example, carbon fiber, a Kevlar-brand material, Dynema-brand material, Aramid-brand material, alloy, glass, binder, epoxy, polyester, acrylic, or any material or combination of materials having a desired strength, stiffness, or flexibility sufficient to reinforce said denture. In one example embodiment, reference posts 206 are made of different material than support bar 202. For example, a support bar 202 may be titanium and reference posts 206 may be anodized titanium. In one embodiment, the reference posts 206 are manufactured separately from the support bar 202 and are utilized in conjunction with the support bar 202 according to the principles described herein.

In some embodiments, a support bar 202 may comprise multiple materials, or any material configuration suitable to enhance or reinforce the resiliency and/or support of the denture when subjected to wear in a wearer's mouth or to satisfy other desired chemical, physical, or biological properties. Furthermore, a support bar 202 may comprise materials with differing grain structures or grain direction or with similar grain structures or grain direction or any grain structure or direction suitable for achieving desired properties in the denture; for example, resiliency under torsional loads.

Figure 7A:
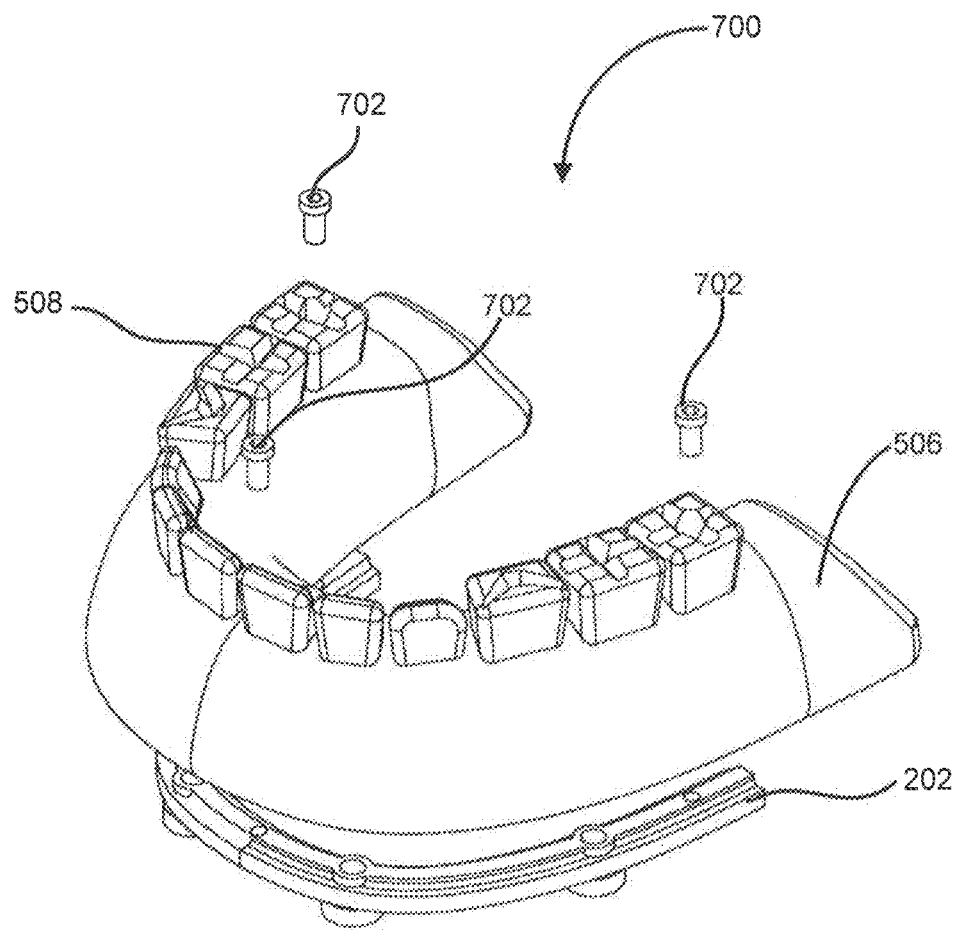
FIG. 7A is a view of an exemplary embodiment of an improved denture having a support bar installed in a denture base by fasteners.
Figure 7B:
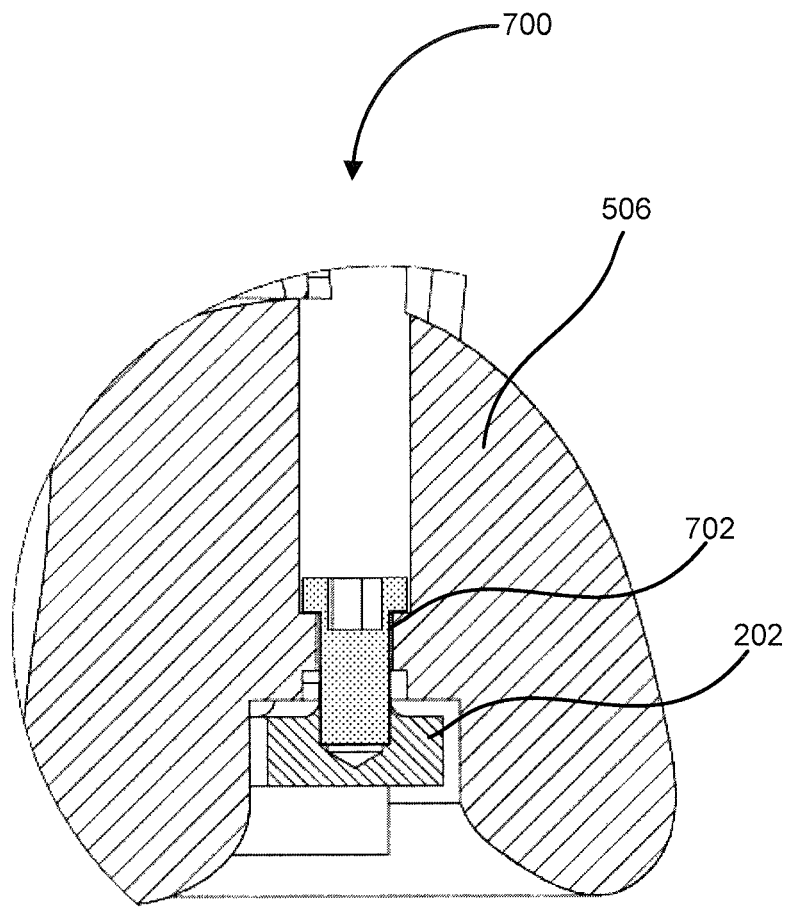
FIG. 7B is a detail view of various aspects of an exemplary embodiment according to FIG. 7A illustrating a fastener and various other components of an improved denture.

Now, having described various components of an improved denture system 600, the assembly of an improved denture system 600 may be appreciated with reference to FIGS. 5A-5D and 6B-6C. In one embodiment, the reference post 206 extending into a corresponding cavity 510 in the artificial denture base 506 is press fit into the corresponding cavity 510. With reference to FIGS. 7A-7B, an alternative embodiment 700 incorporates a screw-retained connection between the support bar 202 and the artificial denture base 506. Still furthermore, in one embodiment of a screw-retained support bar 202, the reference posts 206 do not extend into a corresponding cavity 510 in the artificial denture base 506, but instead, abut at least one face of artificial denture base 506 into which fasteners 702 are inserted. Alternatively, the reference posts 206 are omitted and the denture base 506 and the support bar 202 are referenced and registered via fasteners 702.

Thus, any configuration for connecting reference post 206 and corresponding cavity 510 can be implemented, such as sonic welding, or gluing, or quick-release fittings, or embedding, or any other techniques suitable to accomplish a connection between reference post 206 and corresponding cavity 510. In one embodiment, with reference to FIG. 8, snap-fitting encompasses wherein snap-fit portion 802 of reference post 206 may be permanently installed in corresponding cavities 510 in improved denture base 506, by press fitting. Alternatively, snap-fit portion 802 may be installed by sonic welding, or gluing, or embedding any other mechanism suitable for retaining snap-fit portion 802 of reference posts 206 in corresponding cavities 510. Alternatively, according to FIG. 9, support bar 202 may comprise a snap-fit portion 802 wherein the upper face of support bar 202 comprises a fixed portion 804 and corresponding cavity 510 is shaped to perform the function of snap-fit portion 802 so no snap-fit portion 802 of reference posts 206 is needed.

In one exemplary embodiment, a greater number of corresponding cavities 510 is provided than reference posts 206, for example, so that support bar 202 may optionally be installed in multiple positions or orientations relative to denture base 506. In another example embodiment, a greater number of reference posts 206 than corresponding cavities 510 is provided, for example, so that support bar 202 may be optionally installed in multiple orientations or positions with respect to denture base 506 and the unused reference posts 206 removed. However, any number or configuration of reference posts 206 and corresponding cavities 510 suitable for connecting support bar 202 in proper orientation and position relative to denture base 506 is contemplated.

One exemplary embodiment comprises a support bar 202 joined to an artificial denture base 506 via reference posts 206. Support bar 202 lies in oversize cutout 502 and reference posts 206 protrude into corresponding cavities 510. With momentary reference to FIG. 8, in one embodiment, optional material 806 fills any remaining voids in oversize cutout 502 and corresponding cavities 510 following the insertion of support bar 202.

Now, having described various components of an improved denture system 600 and their assembly, an improved denture may be manufactured according to FIGS. 2A and 6C. An improved denture may be manufactured by a process comprising machining a base 506 wherein the machining forms an oversize cutout 502 in the base 506 and a corresponding cavity 510 in the base 506, inserting a support bar 202 into the oversize cutout 502 and fitting reference posts 206 into corresponding cavity 510, and optionally filling any remaining void of oversize cutout 502 and corresponding cavity 510 with a material.

For example, with reference to FIGS. 5B-5D, an oversize cutout 502 and a corresponding cavity 510 is cut into artificial denture base 506 having simulated dental structures 508. Artificial denture base 506, support bar 202, and simulated dental structures 508 may be made by 3D printing or milling, or any other method of manufacturing, for example, molding or casting. The oversize cutout 502 and corresponding cavity 510 may be made in artificial denture base 506 by milling, or molding, or 3D printing, or any other method for making an improved denture. For example, the oversize cavity and corresponding cutout may be machined by a CAD/CAM machining device, although any process suited for accurate forming of the material may be utilized. For example, said oversize cavity and corresponding cutout may be formed by machining, etching, waterjet, laser cutting, 3D printing, or chemical mask processes.

Turning to FIG. 6A-6C, the process for manufacturing an improved denture system 600 continues with the insertion of bar 202 into oversize cutout 502 and the positioning of reference post 206 in corresponding cavity 510. In one embodiment, a second material (FIG. 8, 806) is optionally filled into any remaining voids in oversize cutout 502 and corresponding cavity 510.

Figure 8:
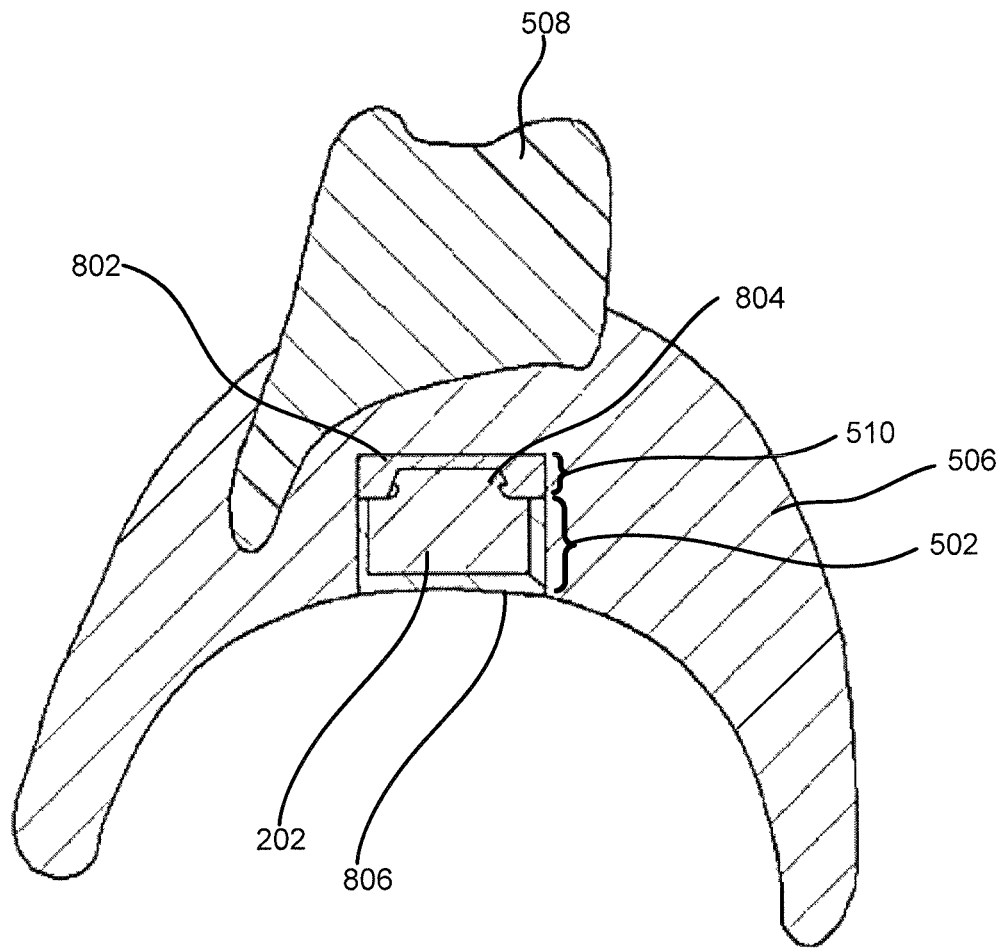
FIG. 8 is a view of an exemplary embodiment of an improved denture having a snap-fit feature.
Figure 9:
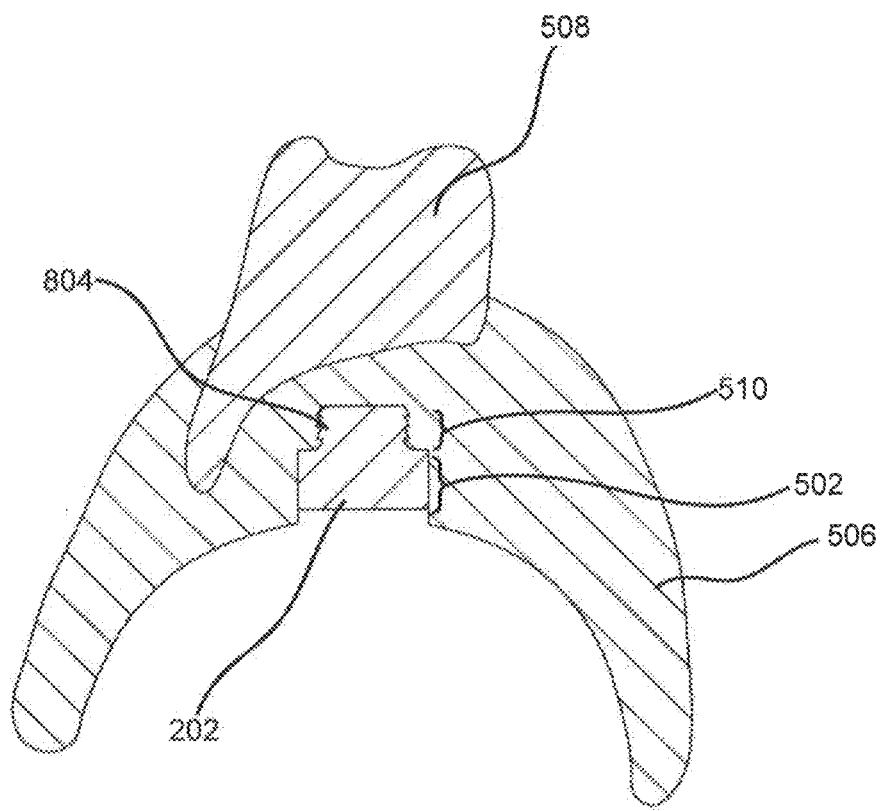
FIG. 9 is a view of an another exemplary embodiment of an improved denture having a snap-fit feature.
Figure 10A:
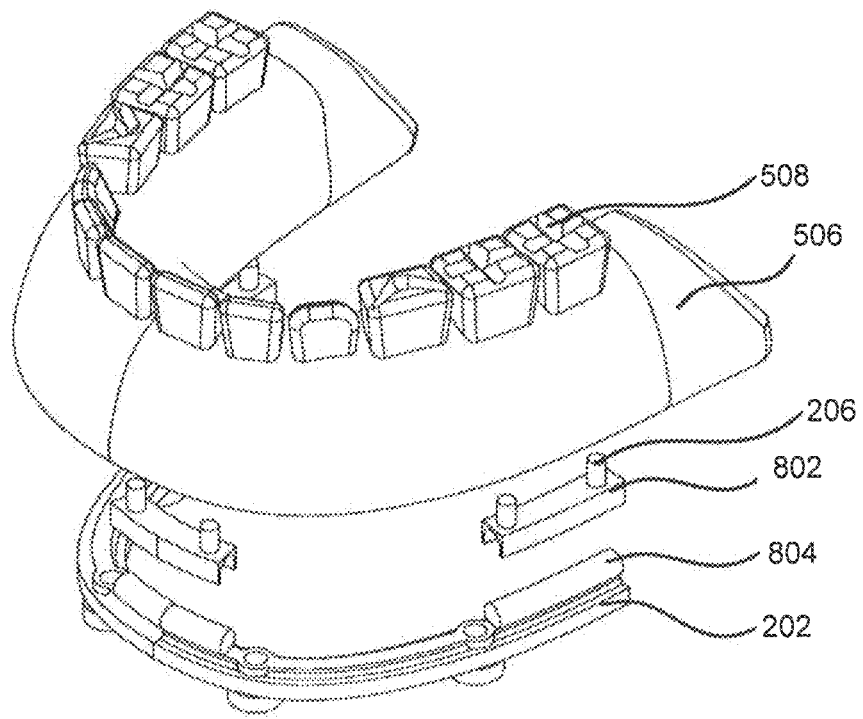
FIG. 10A-10B are views of yet another exemplary embodiment of an improved denture having a snap-fit feature.
Figure 10B:
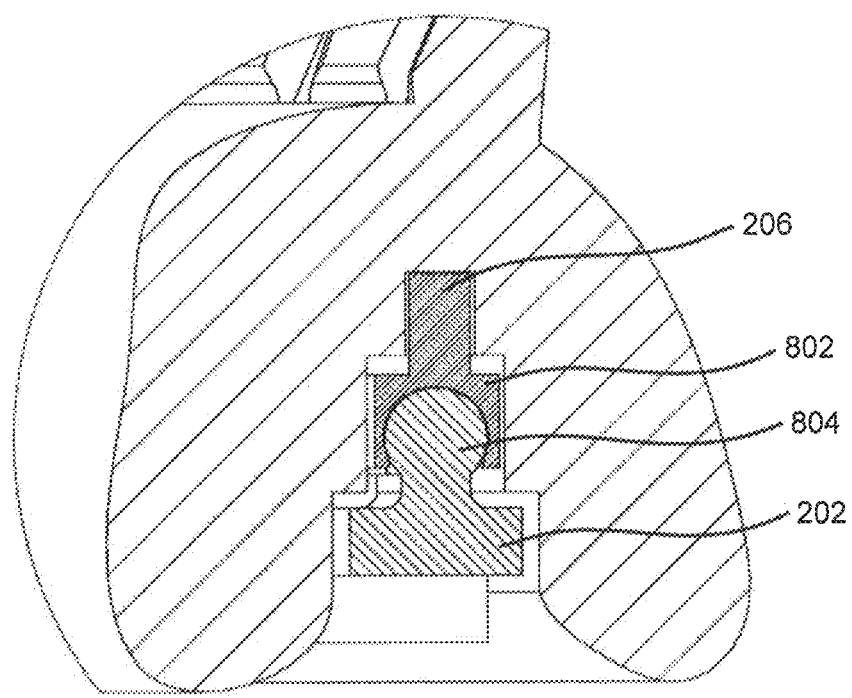

While improved referencing and positioning can be addressed in other embodiments, it would be further advantageous if the support bar 202 were accurately referenced and registered, but also removable via snap-fitting, for example, in order to permit patients to clean their dentures more readily. With reference to FIG. 8-10, an alternative embodiment of an improved denture is disclosed wherein the denture base 506 snap-fits onto bar 202. In one embodiment, reference posts 206 comprise a snap-fit portion 802 and a fixed portion 804. In this embodiment, fixed portion 804 is affixed permanently to bar 202 while snap-fit portion 802 is affixed permanently in corresponding cavity 510. Fixed portion 804 engages with snap-fit portion 802, thereby holding support bar 202 in mechanical communication with artificial denture base 506, yet permitting ready disengagement of snap-fit portion 802 and fixed portion 804 so that the artificial denture base 506 may be disconnected from support bar 202, for example, for removal and cleaning. Generally, support bar 202 lies in oversize cutout 502 of artificial denture base 506 when fixed portion 804 is engaged with snap-fit portion 802. Alternatively, support bar 202 may interface with artificial denture base 506 via any other configuration or mechanism suitable for holding, maintaining, or otherwise coupling or retaining support bar 202 in communication with artificial denture base 506.

Snap-fit portion 802 of reference post 206 may be permanently installed in corresponding cavities 510 in improved denture base 506, by press fitting. Alternatively, snap-fit portion 802 may be installed by sonic welding, or gluing, or embedding any other mechanism suitable for retaining snap-fit portion 802 of reference posts 206 in corresponding cavities 510.

According to FIG. 9, support bar 202 may comprise a snap-fit portion 802 wherein the upper face of support bar 202 comprises a fixed portion 804 and corresponding cavity 510 is shaped to perform the function of snap-fit portion 802 so no snap-fit portion 802 of reference posts 206 is needed. In this embodiment, snap-fit portion 802 of the upper face of support bar 202 interlocks with a corresponding cavity 510 in improved denture base 506. In some embodiments, snap-fit portion 802 traverses the entire length of support bar 202. Alternatively, snap-fit portion 802 may only traverse a portion of the length of support bar 202. In other embodiments, multiple snap-fit portions 802 are spaced along the length of support bar 202, for example, as an alternative embodiment of reference posts 206. Still furthermore, in other example embodiments, a housing is installed into corresponding cavity 510 to receive fixed portion 804 of reference post 206 so no snap-fit portion 802 of reference posts 206 is needed. Zone Name: B1,AMD Still further alternatively, according to FIGS. 10A and 10B, an alternative embodiment of an improved denture is disclosed wherein the denture base 506 snap-fits onto bar 202. According to the principles disclosed herein, support bar 202 may comprise a fixed portion 804 wherein the upper face of support bar 202 comprises a fixed portion 804 and wherein snap-fit portion 802 of reference posts 206 is shaped to attach to fixed portion 804. In one example embodiment, two reference posts 206 share a single snap-fit portion 802. In another example embodiment, each reference post 206 has a snap-fit portion 802. However, any configuration or number of reference posts 206 may share any number or configuration of snap-fit portions 802 so that support bar is held, maintained, or otherwise coupled or retained in communication with artificial denture base 506.

Furthermore, support bar 202 may comprise any number or configuration of fixed portions 804, as disclosed herein. In some embodiments, fixed portion 804 may be cylindrical, or may be oval, or may be asymmetrical or may be any other shape suitable for interfacing with snap-fit portion 802 whereby support bar 202 is held, maintained, or otherwise coupled or retained in communication with artificial denture 506.

In one example embodiment, snap-fit portion 802 further comprises a liner or coating whereby the frictional interface between fixed portion 804 and snap-fit portion 802 may be enhanced. In other embodiments, such a liner or coating may produce an audible click when the fixed portion 804 and snap-fit portion 802 are interfaced, or alternatively snap-fit portion 802 and fixed portion 804 may be configured to produce an audible click when the fixed portion 804 and snap-fit portion 802 are interfaced without need for a liner or coating.

Now, having described various components of an improved denture system wherein the denture base 506 snap-fits onto bar 202, with reference to FIG. 8, an improved denture may be manufactured by a process for manufacturing an improved denture system comprising machining an artificial denture base 506 wherein the machining forms an oversize cutout 502 in the base 506 and a corresponding cavity 510 (shaped to mate with a fixed portion 804) in the base 506, inserting a support bar 202 into the oversize cutout 502 and fitting a fixed portion 804 into the corresponding cavity 510, and optionally, filling any remaining void of oversize cutout 502 and corresponding cavity 510 with a second material 806. In one embodiment, no material is filed into any remaining void and instead, said denture may be optionally removable by the denture user, for example, for cleaning.

An improved denture may be configured to be semi-permanently installed in a patient's mouth, or may be removable. For example, in one embodiment, support bar 202 is snap fit into the improved denture. The support bar 202 may be rigidly affixed to implants in the patient's mouth, so that the denture may be snapped in and out while the support bar 202 remains installed in the patient's mouth. Alternatively, in one exemplary embodiment, the support bar 202 may be permanently affixed to artificial denture base 506, for example, by embedding in optional second material 806, so that the base 506 is configured to be semi-permanently installed in a patient's mouth.

The various components of an improved denture system 600 may be made of various different materials. For example, various materials may be used to manufacture artificial denture base 506. In one exemplary embodiment, a hardened polymethyl methacrylate (PMMA) material is used. However, the denture base 506 may comprise any material having sufficiently low porosity so as to be hygienic for extended placement in a wearer's mouth. For example, the denture may be made of a plastic, ceramic, metal, or acrylic, including for instance, a polymer, monomer, composite, or alloy.

Furthermore, the denture base 506 and any other components of a denture system 600 may be formed according to a process and system for molding or forming products from thermosetting plastics. Such a system may utilize a deformable container that is placed within the cavity of a housing of a mold with resins and initiator mixed therein. As a piston slides into the cavity, the upper edges of the container may engage between the housing and the piston to seal the housing from leakage. The pressure of the piston along with heat on the housing may enable the curing process to be controlled to maximize compression and minimize porosity. Exemplary processes and systems disclosed in U.S. patent application Ser. No. 13/369,238, PROCESSES AND SYSTEMS FOR MOLDING THERMOSETTING PLASTICS are incorporated by reference.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element of any or all the claims.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "proximate," "proximately," or any other variation thereof, are intended to cover a physical connection, an electrical connection, a magnetic connection, an optical connection, a communicative connection, a functional connection, and/or any other connection. When language similar to "at least one of A, B, or C" is used, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. An improved denture system comprising:
    a curved support bar comprising:
        at least one reference post;
        at least one implant interface; and
    a denture base comprising:
        an oversize cutout comprising a unitary channel extending an entire length of said curved support bar and wherein said curved support bar may be placed and wherein said curved support bar only rests against the at least one reference post and not against the oversize cutout;
        at least one corresponding cavity wherein said at least one reference post may be inserted, wherein said corresponding cavity extends farther into said denture base than said oversize cutout; and
        wherein at least a portion of said reference post is fixed in said corresponding cavity by at least one of: screw fasteners, press fitting, snap fitting, and embedding in said denture base,
    whereby said support bar is maintained in substantially fixed communication with said denture base to secure said denture base.

2. The system according to claim 1, wherein said support bar is constrained relative to said denture base in at least one of a 3-2-1 registration, RPS registration, or best-fit registration.

3. The system according to claim 1 wherein said reference post comprises:
    a snap-fit portion affixed permanently to said corresponding cavity;
    a fixed portion affixed permanently to said support bar, said fixed portion and said snap-fit portion selectably engaged to hold said support bar in mechanical communication with said denture base, wherein said support bar lies in said oversize cutout.

4. The system according to claim 1, wherein said denture base is removable from said substantially fixed communication with said support bar.

5. The system according to claim 1, wherein said one or more reference posts comprises one to ten reference posts.

6. The system according to claim 1, wherein said one or more implant interfaces comprises one to ten implant interfaces.

7. The system according to claim 1, wherein said plurality of reference posts are attached to said support bar by threads.

8. The system according to claim 1, wherein said plurality of reference posts and said support bar are a unitary piece of material.

9. A method for providing positioning of a support bar within a denture system, said method comprising:
    providing a curved support bar comprising:
        at least one reference post;
        at least one implant interface;
    providing an improved denture base comprising:
        an oversize cutout comprising a unitary channel extending an entire length of said curved support bar and wherein said curved support bar may be placed, wherein said curved support bar only rests against the at least one reference post and not against the oversize cutout;
        at least one corresponding cavity wherein said at least one reference post may be inserted, wherein said corresponding cavity extends farther into said denture base than said oversize cutout; and
    interfacing at least a portion of said reference post in said corresponding cavity by at least one of: screw fasteners, press fitting, snap fitting, and embedding in said denture base such that said support bar is maintained in substantially fixed communication with said denture base to secure said denture base.

10. The method according to claim 9 wherein said support bar is constrained relative to said denture base in at least one of a 3-2-1 registration, RPS registration, or best-fit registration.

11. The method according to claim 9 wherein said reference post comprises:
    a snap-fit portion affixed permanently to said corresponding cavity;
    a fixed portion affixed permanently to said support bar, said fixed portion and said snap-fit portion selectably engaged to hold said support bar in mechanical communication with said denture base, wherein said support bar lies in said oversize cutout.

12. The method according to claim 9 wherein said denture base is removable from said substantially fixed communication with said support bar.

13. The method according to claim 9 wherein said one or more reference posts comprises one to ten reference posts.

14. The method according to claim 9 wherein said one or more implant interfaces comprises one to ten implant interfaces.

15. The method according to claim 9 wherein said plurality of reference posts are attached to said support bar by threads.

16. The method according to claim 9 wherein said plurality of reference posts and said support bar are a unitary piece of material.

17. A support system comprising:
a bar comprising a single curved segment configured to follow a contour of a patient's edentulous ridge;
a plurality of reference posts extending from the bar and configured to extend into corresponding cavities of a denture base for securement by at least one of: screw fasteners, press fitting, snap fitting, and embedding;
a plurality of implant interfaces disposed along the length of the bar and configured to connect to implants;
wherein the support system is configured to rest in at least one oversize cutout of a denture base forming unitary channel extending an entire length of said support bar to secure said denture base,
wherein the curved support bar is configured to only rest against the plurality of reference posts and not rest against the oversize cutout;
wherein the reference posts configured to extend into corresponding cavities are configured to extend in to corresponding cavities that extend farther into the denture base than the oversize cutout, and
wherein the support bar is configured to be fully constrained by the interfacing of the reference posts and corresponding cavities whereby the support bar is configured to position a denture base in unique fixed position fully constrained relative to the support system.

18. The support system according to claim 17 wherein said plurality of reference posts are attached to said bar by threads.

19. The support system according to claim 18 wherein said bar comprises a different material composition than said plurality of implant interfaces.

* * * * *